(12) United States Patent
Shimada

(10) Patent No.: US 6,582,536 B2
(45) Date of Patent: Jun. 24, 2003

(54) PROCESS FOR PRODUCING STEERABLE SHEATH CATHETERS

(75) Inventor: Jin Shimada, White Bear Lake, MN (US)

(73) Assignee: Biotran Corporation Inc., St. Paul, MN (US)

(*) Notice: Subject to any disclaimer, the term of this patent is extended or adjusted under 35 U.S.C. 154(b) by 0 days.

(21) Appl. No.: 09/833,324

(22) Filed: Apr. 12, 2001

(65) Prior Publication Data

US 2001/0049491 A1 Dec. 6, 2001

Related U.S. Application Data

(60) Provisional application No. 60/199,169, filed on Apr. 24, 2000.

(51) Int. Cl.⁷ ............................................. A61M 25/16
(52) U.S. Cl. .................. 148/519; 148/527; 427/2.3; 264/171.27; 264/171.29; 264/172.15
(58) Field of Search ........................... 148/519, 537; 264/171.27, 171.29, 172.15; 427/2.3

(56) References Cited

U.S. PATENT DOCUMENTS

| | | |
|---|---|---|
| 4,430,083 A | 2/1984 | Ganz et al. |
| 5,527,325 A | 6/1996 | Conley et al. |
| 5,702,373 A | 12/1997 | Samson |
| 5,755,704 A | 5/1998 | Lunn |
| 5,769,830 A | 6/1998 | Parker |
| 5,792,401 A * | 8/1998 | Burnham ............... 264/171.29 |
| 5,820,592 A | 10/1998 | Hammerslag |
| 5,891,112 A | 4/1999 | Samson |
| 5,916,147 A | 6/1999 | Boury |
| 5,951,495 A | 9/1999 | Berg et al. |
| 5,954,651 A | 9/1999 | Berg et al. |
| 5,961,511 A | 10/1999 | Mortier et al. |
| 5,964,971 A | 10/1999 | Lunn |
| 6,017,335 A | 1/2000 | Burnham |
| 6,030,371 A | 2/2000 | Pursley |
| RE36,628 E * | 3/2000 | Sagae et al. ................. 148/537 |
| 6,042,578 A | 3/2000 | Dinh et al. |
| 6,045,734 A | 4/2000 | Luther et al. |
| 6,248,190 B1 * | 6/2001 | Stinson ...................... 148/519 |

\* cited by examiner

*Primary Examiner*—George Wyszomierski
(74) *Attorney, Agent, or Firm*—Kinney & Lange P.A.

(57) ABSTRACT

The invention is a method for manufacturing a steerable catheter having a distal end, proximal end, an outer jacket, a pull wire and a central lumen. The central lumen is maintained in a circular shape without bulges diminishing the useful inter-diameter by using an outer jacket with an elliptical shape and uneven thickness to encase a pull wire. The pull wire friction is also reduced by using one wire of larger diameter to create the lumen for the pull wire of smaller diameter, thus reducing the friction on the pull wire and reducing the locking of the catheter body around the pull wire at bends preventing movement of the pull wire. The distal end of the catheter also has a smooth tip due to heat treating of steel wire braid reinforcement that does not require the addition of bulge forming additional material to control tip shape.

13 Claims, 3 Drawing Sheets

PROCESS FOR PRODUCING STEERABLE SHEATH CATHETERS

This application claims priority from U.S. Provisional patent application Ser. No. 60/199,169 filed on Apr. 24, 2000.

BACKGROUND OF THE INVENTION

This invention relates to catheters which are used to provide access into the human body. More particularly, the present invention is directed to steerable sheath catheters which are used to provide access into the human vasculature for delivery of additional tools, instruments, medications or fluids.

Catheters have been commonly used in medical practice to reach locations inside the body otherwise unreachable without surgery. The body of a catheter is long and tubular and contains an inner lumen. A catheter has a distal end or tip which enters the patient as well as a proximal end that has a handle for control by the operator.

The tip of the catheter is first inserted into a major vein, artery or other body cavity. The catheter is then further inserted and guided to the area of concern. The catheter is often used as a delivery method for other tools, such as balloons for performing angioplasty or a camera for performing endoscopy. As medical knowledge increases, the catheterization procedures have become more complicated and more exacting. The usefulness of catheters is largely limited by the ability to successfully manipulate the position and orientation of the catheter tip into small and tortuous vessels. Therefore the goals for a successful catheter design are to maximize the inner diameter while minimizing the outer diameter and maintaining control and flexibility of the catheter.

One method of directing a catheter into position is through the use of a guide wire. First the guide wire is fed into position within the patient. Then the catheter is urged over the guide wire. However, it is not uncommon for the position of the catheter tip to become dislodged from the desired location as the guide wire is removed.

To avoid this problem, other catheters known in the art, are guided into place without the use of guide wires. These catheters have sufficient pushability that the tip of the catheter can be directed from a proximal location without buckling or kinking. Unfortunately, such guide catheters tend to be more difficult to steer into position and the necessary stiffness can limit their placement in areas with sharp curves.

Catheters with tips preformed into particular shapes specialized for specific applications are known in the art. The pre-shaping of the catheter may aid the placement of the tip in the desired location. However, the pre-shaping of catheters for particular applications requires a hospital to provide a wide array of catheter shapes and sizes for use. Another disadvantage to preformed catheters is that they do not allow the physician to adapt the catheter to account for any peculiarities of a patient's vascular system. A physician can attempt to reshape a catheter before use, by applying heat. However, such manual reshaping is not only time consuming but can compromise the lumen of the catheter, by causing the circular lumen to ovalize or flatten out as the catheter is bent, or even kink or seal at a bend destroying the catheter's usefulness.

Steerable sheath catheters, the present invention being one example, are also directed into position from a proximal location. However, the tips of these catheters are steerable due to the action of one or more pull wires that are embedded along the length of the catheter body. Pre-forming of the catheter is not necessary because the operator can adjust the shape of the catheter or steer the tip as the catheter is directed into the body. Therefore these catheters are capable of use in a wider range of procedures than the specialized preformed catheters.

A current method in the art used to manufacture steerable sheath catheters is to form the catheter on a mandrel using multiple layers: an inner liner, a layer of wire braid and an outer thermoplastic jacket. The inner liner is pulled over the mandrel and tightened down. The pull wire is laid axially along the inner liner, often within a groove present on the surface of the mandrel. The steel braid is pulled or woven over the inner liner and pull wire. After the steel braid is tightened down, the entire catheter is encased in a thermoplastic outer jacket. The outer jacket is then encased in heat shrink material and heated. The heat causes the thermoplastic jacket layer to flow, which when teamed with the pressure from the heat shrink material causes the thermoplastic outer jacket to flow into the steel braid consolidating the catheter into one unit. [U.S. Pat. Nos. 5,669,920; 6,042,578; 5,527,325]

The mandrel in this process usually has a longitudinal groove to facilitate the placement of the pull wire during the manufacturing process. The inner liner of the catheter is placed over the mandrel and is pushed into the groove. The pull wire is then laid in the groove on top of the inner liner. The steel braid and outer jacket can then be pulled easily over the mandrel without disturbing the pull wire. However, the use of this process results in the creation of a bulge in the central lumen. This reduces the useable diameter of the central lumen for the insertion of other instruments. In general, it is desirable to maximize the ratio of the inside diameter to the outer diameter of the tubular body of the catheter.

Another problem in the current art is that by embedding the pull wire through the action of a thermoplastic polymer teamed with a heat shrink material or embedding the wire in the catheter body by spraying the outer jacket material over the wire is that the pull wire creates its own lumen. [U.S. Pat. No. 6,030,371] Therefore the pull wire and its lumen are approximately equal in diameter. This creates three related difficulties. First, there is friction created between the walls of the lumen and the pull wire as an operator attempts to control the catheter by moving the pull wire. The friction increases the difficulty in operating the pull wire. Second, as the catheter is deflected (bent) through the movement of the pull wire, the steel braid embedded in the outer wall of the catheter is also pulled and flexed. As the steel braid flexes, the forces created can deform the lumen. This can cause the steel braid to lock down on the pull wire and its lumen. This greatly increases the friction and can prevent movement of the pull wire as its lumen is deformed from a circular shape into an ovular shape. The third problem is that as the pull wire is "locked down" in the bent catheter, the pull wire and catheter loses the ability to spring back to the original shape as the force on the pull wire from the operator at the proximal end is removed. Accordingly, there remains a need in the art for a catheter with a pull wire with reduced friction and reduced interference from the steel braid which would allow for easier control by the operator and would allow the catheter to spring back into its original shape.

BRIEF SUMMARY OF THE INVENTION

The invention includes a method for manufacturing a steerable catheter having a distal end, a proximal end, an outer jacket, a pull wire and a central lumen having a maximized ration of inner diameter to outer diameter. The central lumen is maintained in a circular shape without bulges diminishing the useful inter-diameter by using an outer jacket with an elliptical shape and uneven thickness to encase a pull wire. The pull wire friction is also reduced by using one wire of larger diameter to create the lumen for the second pull wire of smaller diameter, thus reducing the friction on the pull wire and reducing the locking of the catheter body around the pull wire at bends preventing movement of the pull wire. The distal end of the catheter also has a smooth tip due to heat treating of steel wire braid reinforcement that does not require the addition of bulge forming additional material to control tip shape.

DETAILED DESCRIPTION

Figure 1:
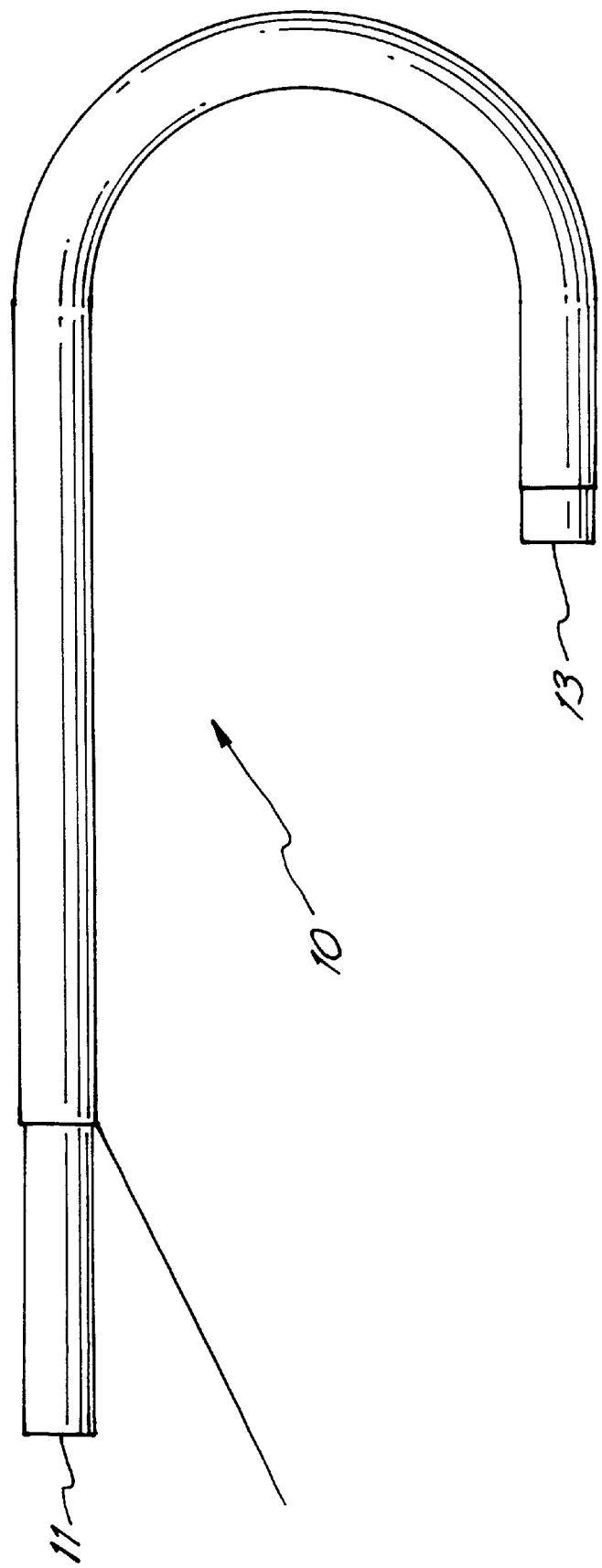
FIG. 1 A perspective view of the catheter.

The present invention provides an improved catheter that maximizes the usable inner diameter and minimizes pull wire friction. The usable inner diameter is maximized compared to the outer diameter by modifying manufacturing techniques. The pull wire is not laid into a groove in the mandrel. Therefore there is no predisposition to form a bulge within the inner lumen of the catheter. Also, the shape of the outer jacket material has been modified from a tube with circular cross-section and uniform thickness to a tube with elliptical or ovular cross-section and uneven thickness. The outer jacket material is thicker at the position of the pull wire. When the outer jacket material is heated until it flows, the material will redistribute around the circumference of the catheter body due to the force of the heat shrink material. The result is an approximately circular catheter with the pull wire embedded within the outer jacket, not protruding into the inner lumen nor bulging out of the outer diameter.

The outer diameter of the catheter is minimized at the tip by a novel treatment method used on the wire braid. The wire braid is formed on a disposable core. An end section of the wire braid is heat tempered and cooled before incorporation into the catheter body. The action of heat tempering the section of wire braid placed at the tip of the catheter releases the stress on the wire and reduces radial forces. Without heat tempering, the wires maintain the stress from being braided, the braid patterns provide radial pressure or outward force at the ends of the braid resulting in a distorted braid pattern. The invention prevents the problem encountered in the prior art of the ends of the wire braid flaring and protruding through the outer jacket of the catheter. In the prior art, the wire braid is contained either through the application of additional material or changing the manufacturing process of the catheter so that the outer jacket material is not heated until fluid. There are problems with both techniques. When additional material is added at the tip of the catheter, an undesirable bulge is formed in that area. If the manufacturing process is changed to deter wire protrusion by incompletely melting the outer jacket material, often the result is incomplete integration and lamination of the catheter, which can result in failure of the catheter.

One alternative method in the prior art would be to heat treat the entire wire braid. However, there is a loss of radial force capacity and the possibility of increased kinking of the wire braid when the entire length of it is heat tempered. Also, the wire will not expand as desired to into the outer jacket material when the outer jacket material is liquefied. The result is a less flexible catheter with possible increased interference between the pull wire and wire braid as well as problems with integrity of the lamination process.

Another method in the prior art to prevent the wire braid from flaring out of the catheter body, is to place an additional piece of polyester around the end of the wire braid. The polyester has a higher melting point than the outer jacket material. Therefore, when the outer jacket material is liquified to allow it to flow into the wire braid, the wire braid remains contained and does not escape from the catheter. The problem with the addition of this additional polyester material is that an undesirable bulge is created on the distal end of the catheter where this additional material is added. An additional problem of poor bonding due to differences in the materials and their melting points can also be seen.

To minimize pull wire friction, the present invention uses one wire in order to create a lumen and then removes that wire and replaces it with a smaller diameter pull wire in order to control the catheter. The benefits of having a pull wire with a smaller diameter than the lumen is to allow easier movement of that pull wire through the reduced friction of contact between the lumen and the pull wire. An additional benefit is that as the catheter is bent, there is additional space inside the lumen, so as the wire braid is pulled, thereby placing force onto the lumen, the pull wire will not become as easily locked down by the changed shape of the lumen. If the pull wire is the same size as the lumen as it is in prior art applications, the wire braid can lock down the pull wire and prevent its movement as the lumen is deformed from a circular shape into an ovular shape. This problem may require a catheter to have multiple pull wires just to allow the catheter to move in one plane. If a pull wire in the current art becomes locked down as the catheter is bent, operation of a pull wire on the opposite side is necessary to return the catheter to its original straight configuration. In the current invention, because the lumen is larger than the pull wire, forces placed on the lumen by the wire braid are much less likely to lock down the pull wire and preventing its free movement and control of the catheter. Therefore, the inventive catheter can return to its original straight configuration simply by releasing the force on the pull wire. In summary, the inventive catheter allows you to have a pull wire with free movement without any loss in internal or external space and also has increased flexibility because the braid will not lock up the pull wire.

FIG. 1 illustrates the basic structure of a catheter generally indicated at 10 made in accordance with the present invention. The catheter 10 extends from a proximal end 11 to a distal end 13. The proximal end 11 is handled by the operator, while the distal end 13 contains the catheter tip which is inserted into the body. The overall length of the catheter may be varied as necessary for various applications. Typical catheter lengths will be on the order of 20–60 inches, with a preferred length of 48 inches.

Figure 2:
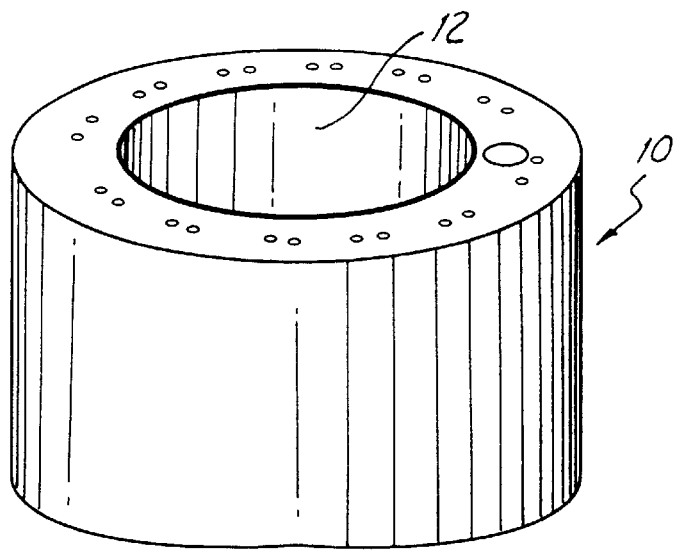
FIG. 2 A perspective view of the catheter body.

The catheter 10 is generally tubular in shape and desirably includes a central lumen 12 as seen in FIG. 2. As is known in the art, alternative embodiments include more than one lumen or subdividing a large lumen into two or more separate lumens, such as in balloon angioplasty.

Figure 3:
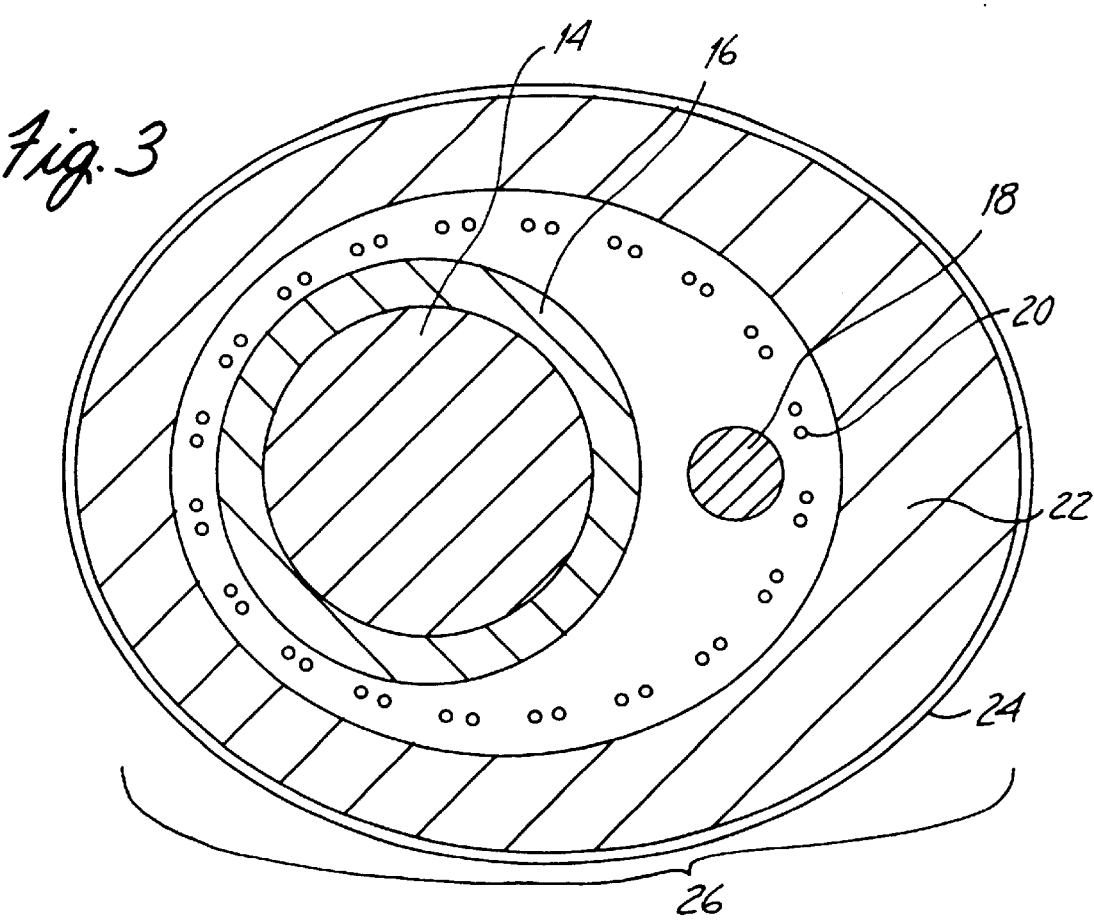
FIG. 3 A cross-sectional view of the catheter assembly before lamination by heating.

The basic method of manufacture according to a first embodiment of the present invention will be described below and as seen in FIG. 3. The catheter components as they are assembled will be collectively referred to as a catheter assembly 26. A ground mandrel 14, which is preferably approximately 4 feet in length, is the first component of the catheter assembly 26. The mandrel 14 has two ends named for reference the distal and the proximal ends. The inner liner 16 is placed on the mandrel 14. The inner liner 16 is preferably an extruded Teflon® (polytetrafluoroethylene) tubing, which is available commercially. The inner liner 16 is knotted at one end (e.g. the distal end 13 shown in FIG. 1) and is fed on to the mandrel 14. It is snugged down by pulling and knotted on the other end (e.g. the proximal end 11 shown in FIG. 1) also.

A lumen defining wire 18, is placed longitudinally along the inner liner 16. The lumen defining wire 18, is composed of stainless steel and is 0.010 inches in diameter. In the preferred embodiment, the lumen defining wire 18 is encased inside another preformed Teflon® tube before placement along the inner liner. In alternative embodiments the lumen defining wire 18 may be covered with other lubricious materials before placement, an example being coating the lumen defining wire with silicone.

A wire braid 20, which is either purchased separately or braided on site, is formed onto disposable core material in order to achieve the proper diameter. The wire braid 20 is preferably composed of φ0.003 high tensile stainless steel wire. The wire braid 20 is formed in a standard braid pattern with preferably approximately 16 wires at 45–60PPI. Before the wire braid 20 is placed onto the catheter assembly 26, one end is heat tempered with a torch or alternate heat source. The wire braid 20 is cooled, removed from the disposable core material and carefully slid over the catheter assembly 26. It is necessary that care is taken not to disturb the position of the lumen defining wire 18, which must remain straight. The end of the wire braid which has been heat treated or annealed terminates somewhat before the distal end 13 of the mandrel 14. The untreated end of the wire braid 20 is knotted at the proximal end 11 of the mandrel 14. Therefore, at the distal end 13 of the assembly both the inner liner 16 and the lumen defining wire 18 are exposed.

An outer jacket 22 is slid over the catheter assembly 26. The outer jacket 22 is a tube extruded from Pebax® before application to the catheter assembly 26. Pebax® is a thermoplastic elastomer resin by the ATOCHEM Corporation of France. The outer jacket 22 is made of either single or multiple sections of tubing that are butted together over the catheter assembly 26 leaving the distal end of the wire braid 20 exposed. Different sections of the outer jacket 22 may have different softness/stiffness (tensile) characteristics in order to facilitate particular features in the catheter. For example, a bending region may have an outer jacket section that has greater softness than a region that will remain straight.

In the preferred embodiment, a tube of heat shrink material 24 is placed over the top of the outer jacket 22. The heat shrink material 24 is a fluoropolymer or polyolefin material. FIG. 3 displays a cross-section of the catheter assembly 26 before lamination of the materials by heating.

Next, the entire catheter assembly 26 is laminated by heating until the outer jacket 22 liquefies. The heat shrink material 24 has a higher melt temperature that the outer jacket 22 and when it constricts the heat shrink material retains its tubular shape thereby forcing the liquefied outer jacket 22 into the wire braid and into contact with the lumen defining wire 18 and inner liner 16. The catheter assembly 26 is cooled and the outer jacket 22 solidifies. The heat shrink material 24 is scored and cracked open in order to remove it. After removal, the outer jacket 22 becomes the outside layer of the catheter.

In alternative embodiments the catheter assembly 26 may be laminated using alternative techniques. In one embodiment, after the outer jacket 22 is slid over the catheter assembly 26, the catheter assembly 26 may be laminated using heat in conjunction with a press that has a mold for defining the final shape of the catheter. Another embodiment applies the outer jacket 22 by extruding the material over the catheter assembly 26.

Figure 4:
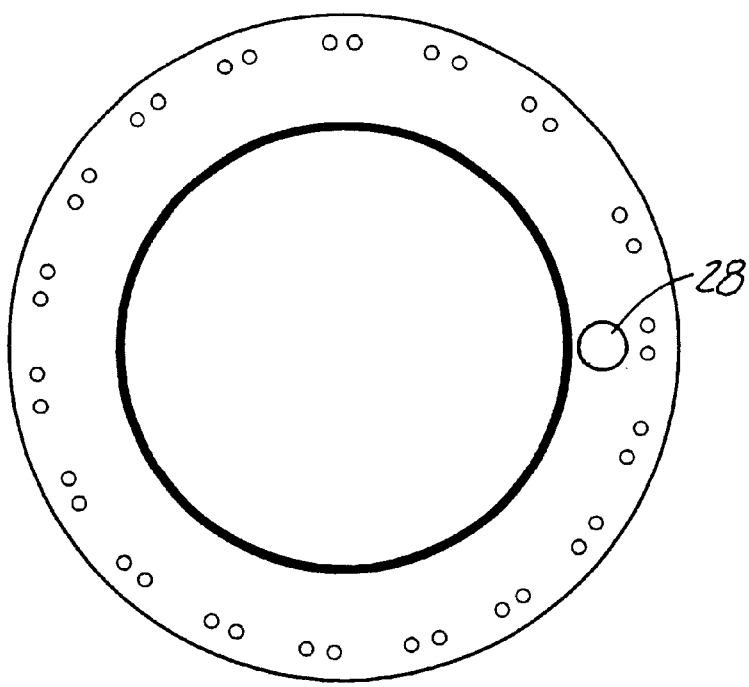
FIG. 4 A cross-sectional view of the catheter assembly after lumen-defining wire is removed.
Figure 5:
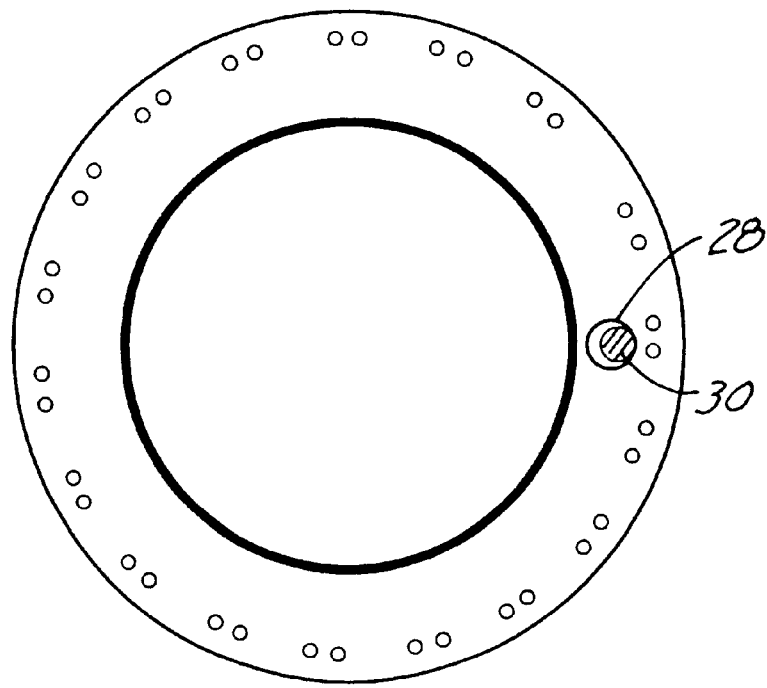
FIG. 5 A cross-sectional view of the catheter assembly after insertion of pull wire into the lumen.

Next the lumen defining wire 18 is removed from the distal end and removed from the catheter assembly 26. A lumen 28 for placement of a pull wire 30 remains in the outer jacket 22 as displayed in FIG. 4. A permanent pull wire 30 is inserted into this lumen 28 from the distal end of the catheter assembly 26 as displayed in FIG. 5. At the end of the pull wire 30 is attached to a pull ring which is placed around the distal end of the catheter assembly 26. The permanent pull wire has a diameter of preferably approximately 0.008 inches. The diameter of the permanent pull wire 30 is smaller than the lumen defining wire 18. Alternate embodiments include coating the permanent pull wire 30 with Teflon®, marketed by E.I. dupont de Nemours and Company Corporation of Wilmington, Del., or other lubricious materials, such as silicones so that the wire is more easily moved within the lumen.

After the permanent pull wire 30 and attached pull ring are in place, another section of outer jacket made from Pebax® is placed on the distal end of the catheter assembly 26, over the exposed mandrel, permanent pull wire, pull ring and annealed wire braid. This distal end section of Pebax® material is also covered with heat shrink tubing and is heated until the Pebax® material is liquified. When liquified, this distal end section flows to connect with the main section of outer jacket and captures the pull ring of the permanent guide wire. After heating is complete and the catheter is cooled, the pull ring is secured by the Pebax® polymer and the heat shrink tubing is once again removed. The mandrel is removed from the completed catheter body which is ready for installation of a handle on the proximal end.

Although the present invention has been described with reference to preferred embodiments, workers skilled in the art will recognize that changes may be made in form and detail without departing from the spirit and scope of the invention.

What is claimed is:

1. A method to manufacture a steerable sheath catheter, the catheter including an outer jacket and a pull wire embedded into the outer jacket, comprising:

laminating the outer jacket to surround a lumen defining wire;

removing the lumen defining wire thereby forming a lumen; and inserting a pull wire into the lumen, wherein the pull wire has a smaller diameter than the lumen.

2. A method of claim 1 wherein the catheter includes an inner liner.

3. A method of claim 1 wherein the lumen defining wire has a diameter of approximately 0.010 inches.

4. A method of claim 1 wherein the pull wire has a diameter of approximately 0.008 inches.

5. The method of claim 1 wherein the lumen defining wire is coated with a lubricious material.

6. The method of claim 1 wherein the outer jacket is made of a heat flowable polymer.

7. In a process for making a steerable catheter wherein the catheter has an inner liner, a braided wire, an outer jacket and a pull wire, the improvement comprising:

inserting a lumen defining wire between the inner liner and the outer jacket;

annealing the inner liner, the braided wire and the outer jacket into a catheter sheath;

removing the lumen defining wire thereby forming a lumen; and inserting a pull wire into the lumen, wherein the pull wire has a diameter smaller than the diameter of the lumen defining wire.

8. The process of claim 7 wherein the braided wire is disposed between the lumen and the outer jacket.

9. The process of claim 7 wherein the inner liner is composed of fluorocarbon polymer.

10. A method to manufacture a steerable sheath catheter, the method including placing an inner liner over a mandrel, placing a pull wire on the inner liner, placing a wire braid over the inner liner and pull wire, placing an outer jacket over the wire braid, pull wire and liner, deforming the outer jacket with heat into a uniformly circular outer cross-sectional shape, the improvement comprising:

utilizing an outer jacket wherein the outer jacket is thicker at one cross-sectional portion and thinner at another cross-sectional portion;

positioning the outer jacket over the wire braid and pull wire so that the thicker cross-sectional portion is over the pull wire.

11. The method of claim 10 wherein the outer jacket is thicker at one cross-sectional portion and thinner at another cross-sectional portion approximately 180° therefrom.

12. In a process for making a steerable catheter wherein the catheter has an inner liner, a wire braid, an outer jacket and a pull wire, the improvement comprising:

extruding the outer jacket, wherein the jacket is thicker at one cross-sectional portion and thinner approximately 180° therefrom;

disposing a pull wire between the inner liner and the thicker cross-sectional portion of the outer jacket; and deforming the outer jacket with heat into a circular outer cross-sectional shape.

13. In a process for making a steerable sheath catheter, the process including:

placing an inner liner over a mandrel, placing a pull wire longitudinally along the inner liner, placing a wire braid over the inner liner and pull wire, placing an outer jacket over the wire braid, and laminating the catheter by applying heat, the improvement comprising:

placing the wire braid onto a disposable core material;

heat treating an end portion of the wire braid;

removing the disposable core material; and placing the wire braid over the inner liner and pull wire.

* * * * *